US011273251B2

(12) United States Patent
Ogawa et al.

(10) Patent No.: US 11,273,251 B2
(45) Date of Patent: Mar. 15, 2022

(54) MEDICAL EQUIPMENT PACKAGE

(71) Applicant: TERUMO KABUSHIKI KAISHA, Tokyo (JP)

(72) Inventors: Junichi Ogawa, Yamanashi (JP); Yoshikazu Kotani, Yamanashi (JP); Kazunori Koiwai, Kanagawa (JP); Takehiro Ura, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/282,187

(22) Filed: Feb. 21, 2019

(65) Prior Publication Data
US 2019/0175817 A1 Jun. 13, 2019

Related U.S. Application Data

(63) Continuation of application No. PCT/JP2017/029865, filed on Aug. 22, 2017.

(30) Foreign Application Priority Data

Aug. 23, 2016 (JP) .............................. JP2016-162863

(51) Int. Cl.
*A61M 5/28* (2006.01)
*A61M 5/34* (2006.01)
(Continued)

(52) U.S. Cl.
CPC .............. *A61M 5/002* (2013.01); *A61M 5/00* (2013.01); *A61M 5/28* (2013.01); *A61M 5/347* (2013.01);
(Continued)

(58) Field of Classification Search
CPC .......... A61M 5/00; A61M 5/002; A61M 5/28; A61M 5/3134; A61M 5/315;
(Continued)

(56) References Cited

U.S. PATENT DOCUMENTS 2,851,188 A * 9/1958 Pavelle ................. G03B 21/64
                                                        206/558
3,107,785 A * 10/1963 Rochr ................. A61M 5/3205
                                                        206/365
(Continued)

FOREIGN PATENT DOCUMENTS

JP      2000-271219 A    10/2000
JP      2006-016053 A     1/2006
(Continued)

OTHER PUBLICATIONS

International Searching Authority, "International Search Report," issued in connection with International Patent Application No. PCT/JP2017/029865, dated Sep. 19, 2017.
(Continued)

*Primary Examiner* — Bryon P Gehman
(74) *Attorney, Agent, or Firm* — Foley & Lardner LLP

(57) ABSTRACT

A medical equipment package containing a plurality of prefilled syringe systems includes: a plurality of syringe packaging bodies, each comprising a packaging main body that accommodates one of the prefilled syringe systems; and an outer box that accommodates the plurality of syringe packaging bodies. Each prefilled syringe system includes: a prefilled syringe, a needle packaging body including: a needle unit that comprises a needle body configured to puncture a living body, and a needle hub that holds the needle body, and a needle unit case that accommodates the needle unit. The needle unit is supported with respect to the needle unit case such that a largest outer diameter portion provided on a tip end side of the needle hub engages with an inner surface of the needle unit case.

8 Claims, 16 Drawing Sheets

(51) Int. Cl.
*A61M 5/31* (2006.01)
*A61M 5/32* (2006.01)
*A61M 5/00* (2006.01)

(52) U.S. Cl.
CPC ......... *A61M 5/3134* (2013.01); *A61M 5/3204* (2013.01); *A61M 5/3293* (2013.01)

(58) Field of Classification Search
CPC .. A61M 5/31505; A61M 5/32; A61M 5/3204; A61M 5/3293; A61M 5/347; B65D 25/04; B65D 81/24; B65D 83/10
USPC ............... 206/365, 36, 370, 459.5, 526, 366
See application file for complete search history.

(56) References Cited

U.S. PATENT DOCUMENTS

| | | | | |
|---|---|---|---|---|
| 3,941,303 A | * | 3/1976 | Wilbur | B65D 5/5405 |
| | | | | 206/526 |
| 3,979,046 A | * | 9/1976 | Wilbur | B65D 5/0227 |
| | | | | 206/526 |
| 4,214,659 A | * | 7/1980 | Jaeschke | B65D 5/0254 |
| | | | | 206/365 |
| 6,554,135 B1 | * | 4/2003 | Luceri | B65D 5/5445 |
| | | | | 206/526 |
| 8,728,028 B2 | * | 5/2014 | Jeter | A61M 5/002 |
| | | | | 206/370 |
| 8,925,723 B2 | * | 1/2015 | Folchini | A61M 5/008 |
| | | | | 206/364 |
| 2014/0224688 A1 | * | 8/2014 | Slemmen | A61M 5/3204 |
| | | | | 206/365 |

FOREIGN PATENT DOCUMENTS

| | | |
|---|---|---|
| JP | 2013-013581 A | 1/2013 |
| JP | 5756793 B2 | 7/2015 |
| WO | WO-2012/157313 A1 | 11/2012 |
| WO | WO-2016/021650 | 2/2016 |

OTHER PUBLICATIONS

International Searching Authority, "Written Opinion," issued in connection with International Patent Application No. PCT/JP2017/029865, dated Sep. 19, 2017.
Extended European Search Report dated Apr. 29, 2020 in corresponding European Patent Application No. 17843558.2.
Office Action dated Apr. 20, 2021 issued in Japanese Patent Application No. 2018-535680, (6 pages).

* cited by examiner

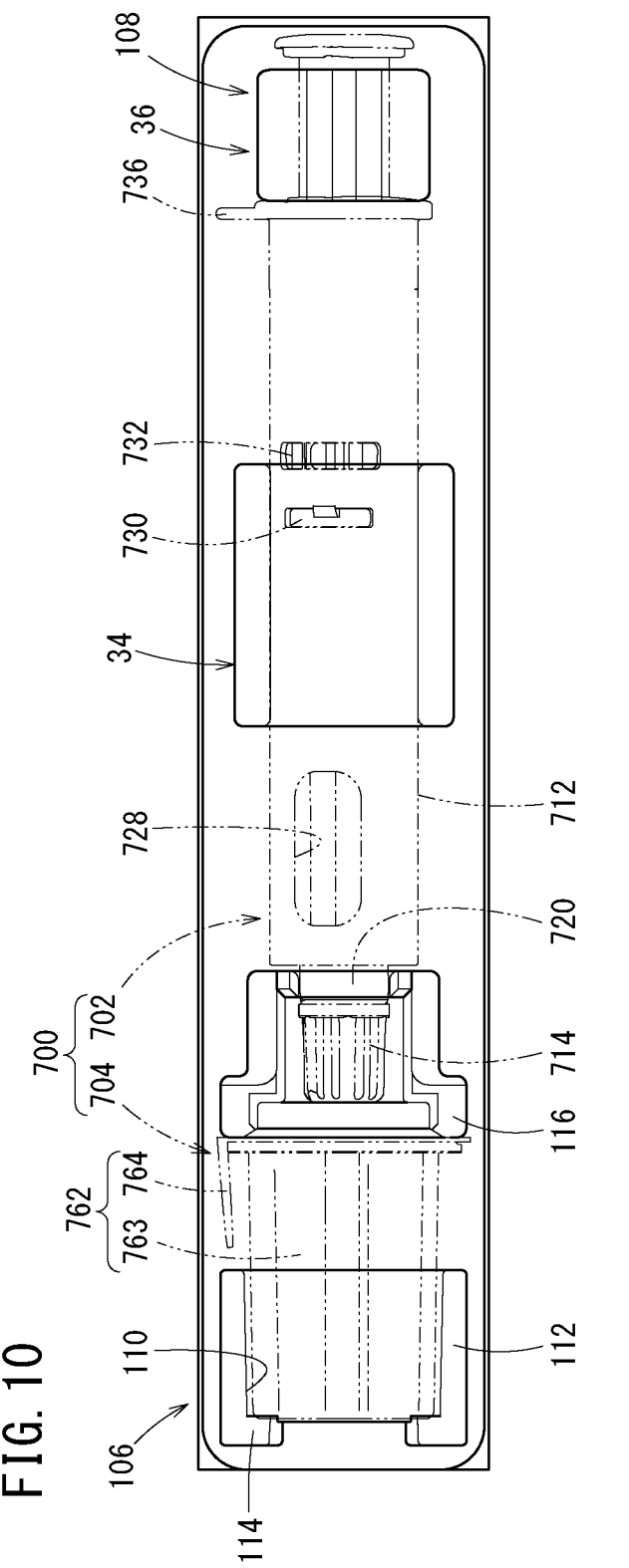
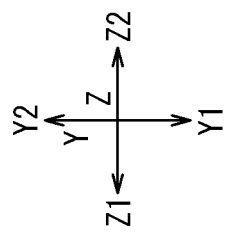

FIG. 11
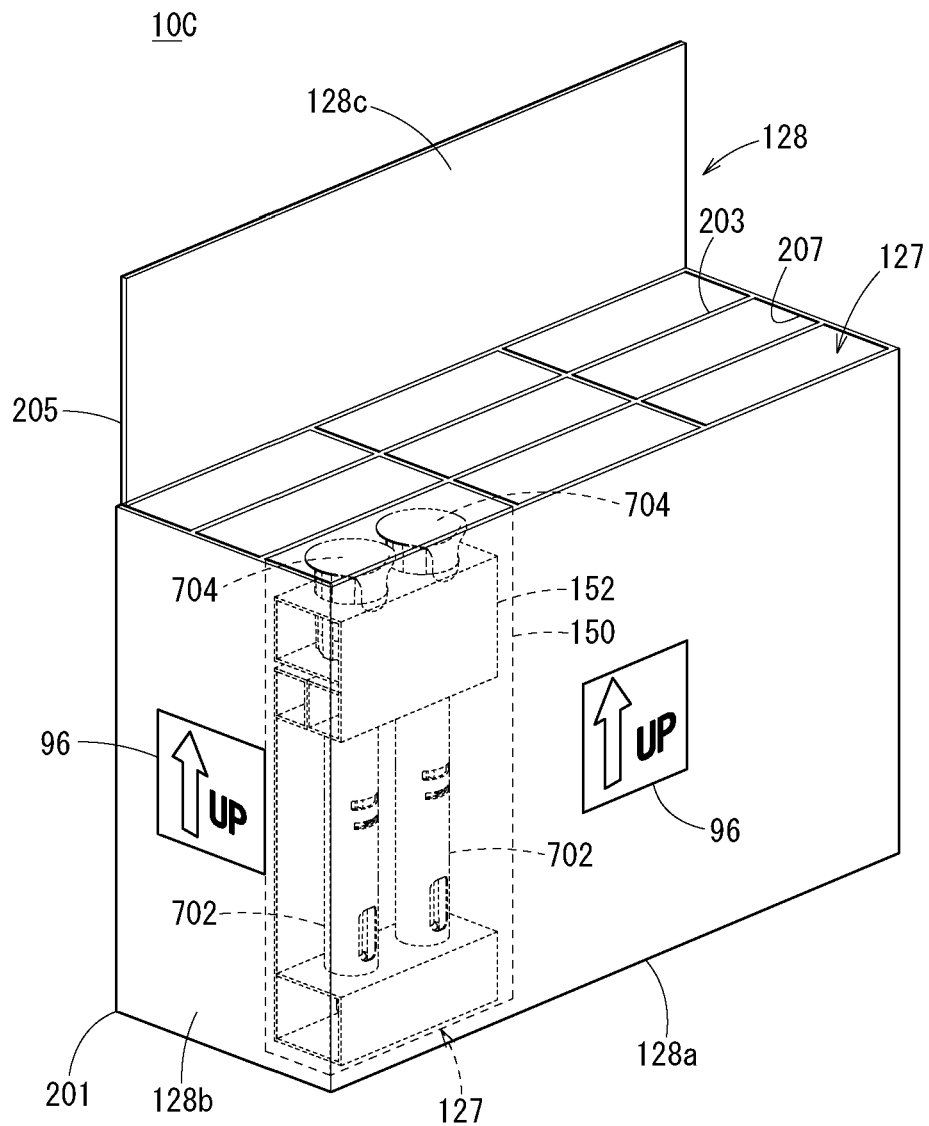
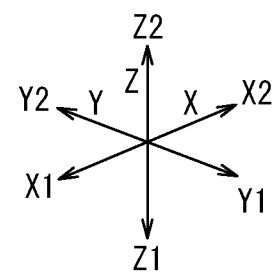

MEDICAL EQUIPMENT PACKAGE

CROSS-REFERENCE TO RELATED APPLICATIONS

This is a bypass continuation of PCT Application No. PCT/JP2017/029865, filed on Aug. 22, 2017, which claims priority to Japanese Application No. 2016-162863, filed on Aug. 23, 2016. The contents of these applications are hereby incorporated by reference in their entireties.

BACKGROUND

The present disclosure relates to a medical equipment package provided with a plurality of syringe packaging bodies including a prefilled syringe system including a prefilled syringe and a needle unit and a packaging main body that accommodates the prefilled syringe system and an outer box that accommodates a plurality of syringe packaging bodies.

For example, Japanese Patent No. 5756793 discloses a prefilled syringe system in which a prefilled syringe and a needle unit are separated from each other. The needle unit accommodated in a needle unit case to form a needle packaging body includes a needle body capable of puncturing a living body and a needle hub that holds the needle body, and is fixed in the needle unit case with a largest outer diameter portion provided on a tip end side of the needle hub fitting to an inner surface of the needle unit case.

SUMMARY

When transporting the prefilled syringe system described above, a syringe packaging body is prepared by accommodating the prefilled syringe system in a packaging main body. Then, a plurality of syringe packaging bodies are accommodated in an outer box, and the outer box is transported.

In this case, when the syringe packaging body is arranged in the outer box such that the needle body of the needle unit extends in a direction orthogonal to an up-and-down direction of the outer box, there is a possibility that the needle unit is unfixed from the needle unit case in a case where an impact in a vertical direction is applied to the outer box at the time of transportation.

Certain embodiments of the present invention have been developed in consideration of such a problem, and an object thereof is to provide a medical equipment package capable of inhibiting the needle unit from being unfixed from the needle unit case when an impact in the vertical direction is applied to the outer box at the time of transportation.

In one embodiment, a medical equipment package is provided with a plurality of syringe packaging bodies each including a prefilled syringe system including a prefilled syringe and a needle unit and a packaging main body that accommodates the prefilled syringe system, and an outer box that accommodates the plurality of the syringe packaging bodies, in which the prefilled syringe system includes a needle packaging body provided with the needle unit including a needle body capable of puncturing a living body and a needle hub that holds the needle body and a needle unit case that accommodates the needle unit, the needle unit is supported with respect to the needle unit case with a largest outer diameter portion provided on a tip end side of the needle hub engaging with an inner surface of the needle unit case, and the plurality of syringe packaging bodies is arranged in the outer box such that an axial direction of the needle body is in an up-and-down direction of the outer box.

According to such a configuration, because the axial direction of the needle body is in the up-and-down direction of the outer box, the axial direction of the needle body is in the vertical direction at the time of transportation. Therefore, it is possible to inhibit the needle unit from being unfixed from the needle unit case when an impact in the vertical direction is applied to the outer box at the time of transportation.

In one aspect of the above-described medical equipment package, the plurality of syringe packaging bodies are arranged in the outer box such that a needle tip of the needle body faces a lower part of the outer box.

With such a configuration, it is possible to effectively inhibit the needle unit from being unfixed from the needle unit case when the outer box drops.

In one aspect of the above-described medical equipment package, the syringe packaging body includes the packaging main body and a supporting unit arranged in the packaging main body to support the prefilled syringe system.

With such a configuration, positional shift of the needle unit case with respect to the packaging main body may be inhibited.

In one aspect of the above-described medical equipment package, the supporting unit includes a needle unit case supporting unit that supports the needle unit case and a base portion that holds a position of the needle unit case supporting unit in the packaging main body.

With such a configuration, positional shift of the needle unit case with respect to the packaging main body may be inhibited with a simple configuration.

In one aspect of the above-described medical equipment package, the needle unit case supporting unit restricts displacement of the needle unit case in a direction orthogonal to the axial direction of the needle body with respect to the packaging main body.

With such a configuration, it is possible to inhibit the needle unit case from falling so that the axis of the needle body is in a horizontal direction within the packaging main body due to vibration and the like at the time of transportation.

In one aspect of the above-described medical equipment package, a display unit displaying the up-and-down direction of the outer box at the time of transportation is provided on an outer surface of the outer box.

With such a configuration, the axial direction of the needle body may be surely made in the vertical direction at the time of transportation.

According to certain embodiments of the present invention, because the axial direction of the needle body is in the up-and-down direction of the outer box, it is possible to inhibit the needle unit from being unfixed from the needle unit case when an impact in the vertical direction is applied to the outer box at the time of transportation.

BRIEF DESCRIPTION OF THE DRAWINGS

FIG. 10 is a plan explanatory view of a supporting unit illustrated in FIG. 9.

FIG. 11 is a perspective view of a medical equipment package according to a third embodiment of the present invention.

DETAILED DESCRIPTION

Embodiments of a syringe packaging body according to the present invention are hereinafter described with reference to the accompanying drawings.

First Embodiment

Figure 1:
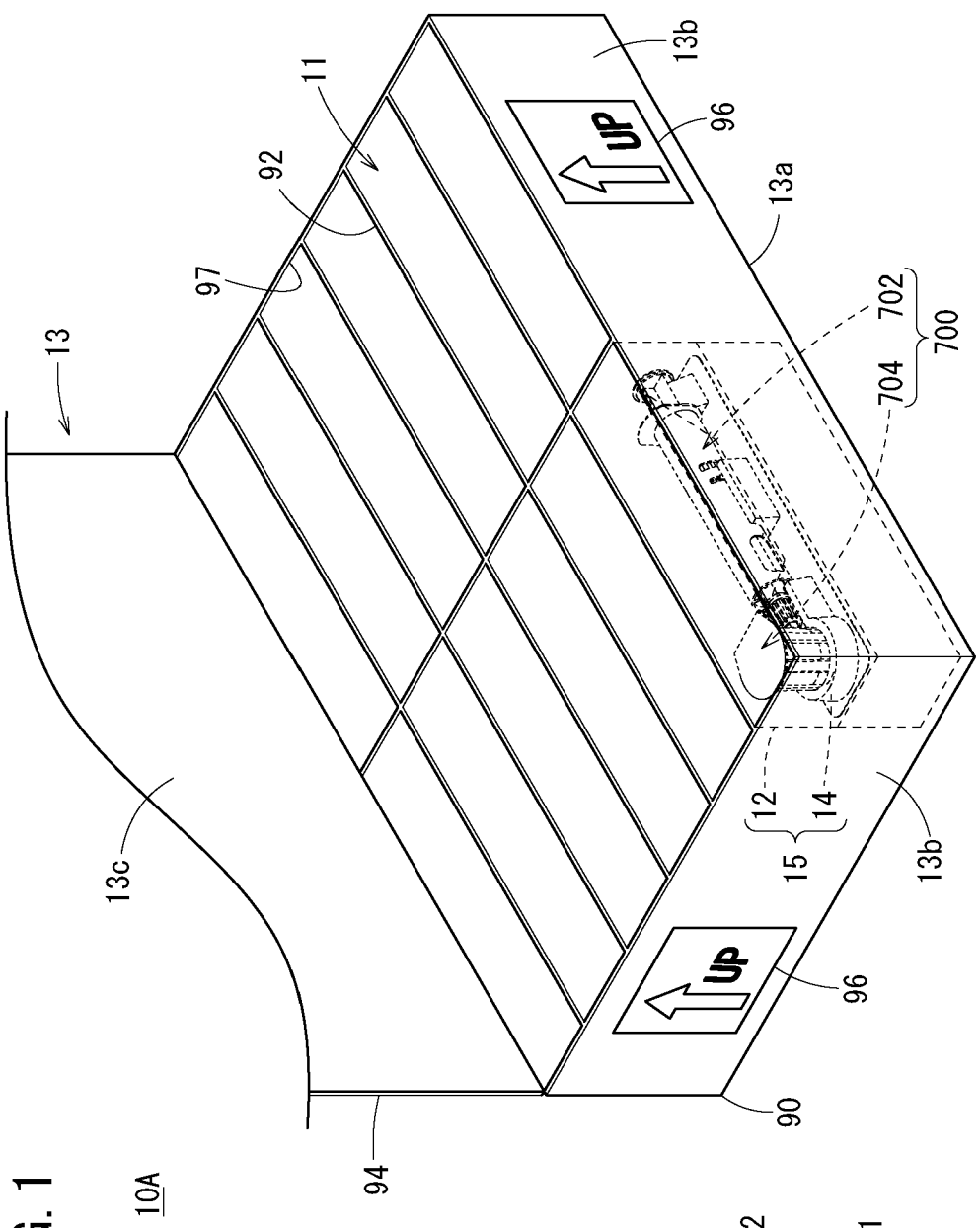
FIG. 1 is a perspective view of a medical equipment package according to a first embodiment of the present invention.
Figure 2:
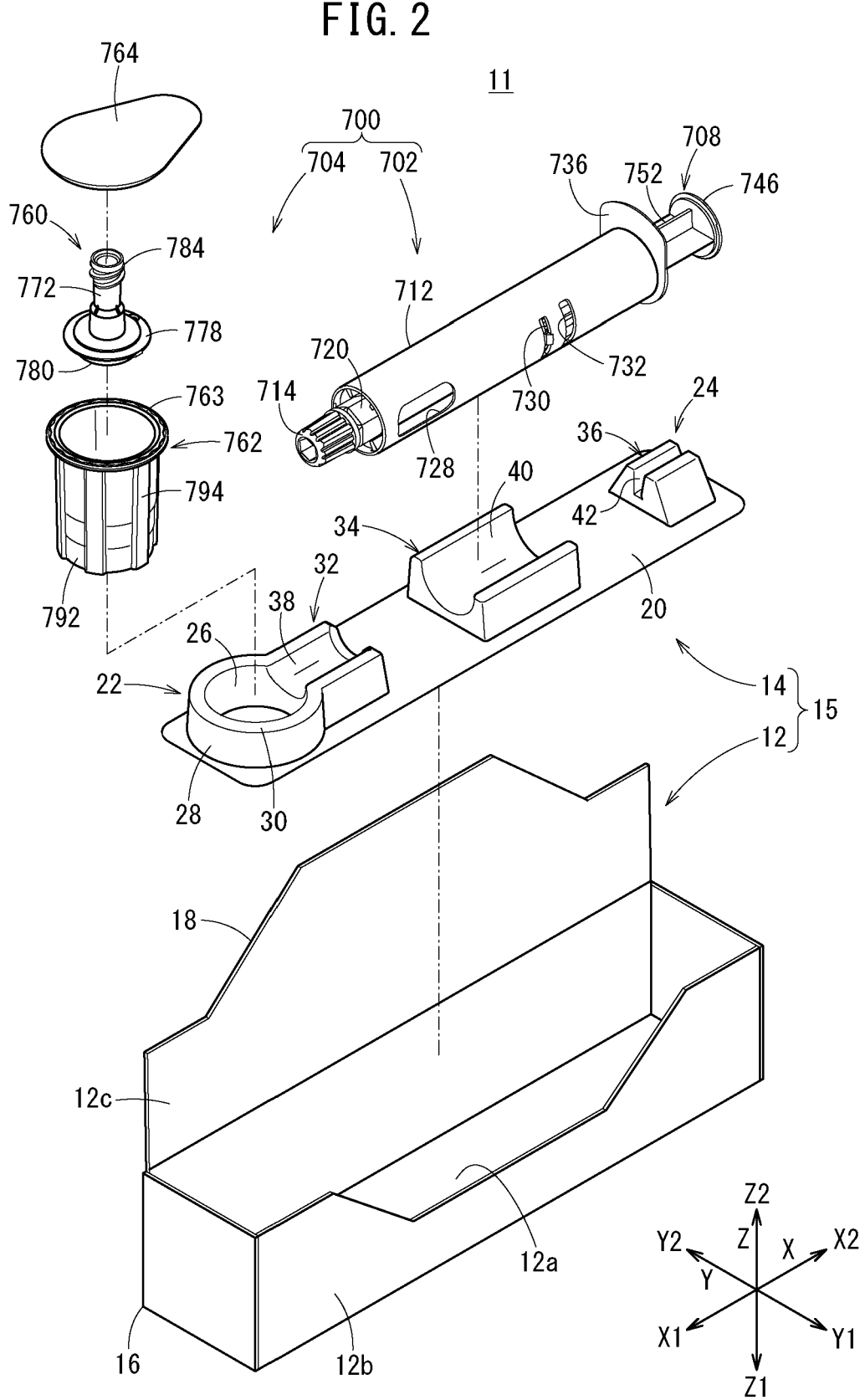
FIG. 2 is an exploded perspective view of a syringe packaging body forming the medical equipment package.

As illustrated in FIG. 1, a medical equipment package 10A according to a first embodiment of the present invention is provided with an outer box 13 as a package box that accommodates a plurality of syringe packaging bodies 11. As illustrated in FIG. 2, the syringe packaging body 11 includes a prefilled syringe system 700 and a packaging unit 15 that accommodates the prefilled syringe system 700.

The prefilled syringe system 700 is first described. The prefilled syringe system 700 is a device for administering a vaccine (drug) against influenza and the like subcutaneously or intradermally, for example, and is provided with a prefilled syringe 702 and a needle packaging body 704 including a needle unit 760. Specifically, when not in use, the prefilled syringe system 700 is kept in a state in which the prefilled syringe 702 and the needle unit 760 are separated from each other, and the needle unit 760 of the needle packaging body 704 is mounted on the prefilled syringe 702 when used.

Figure 3:
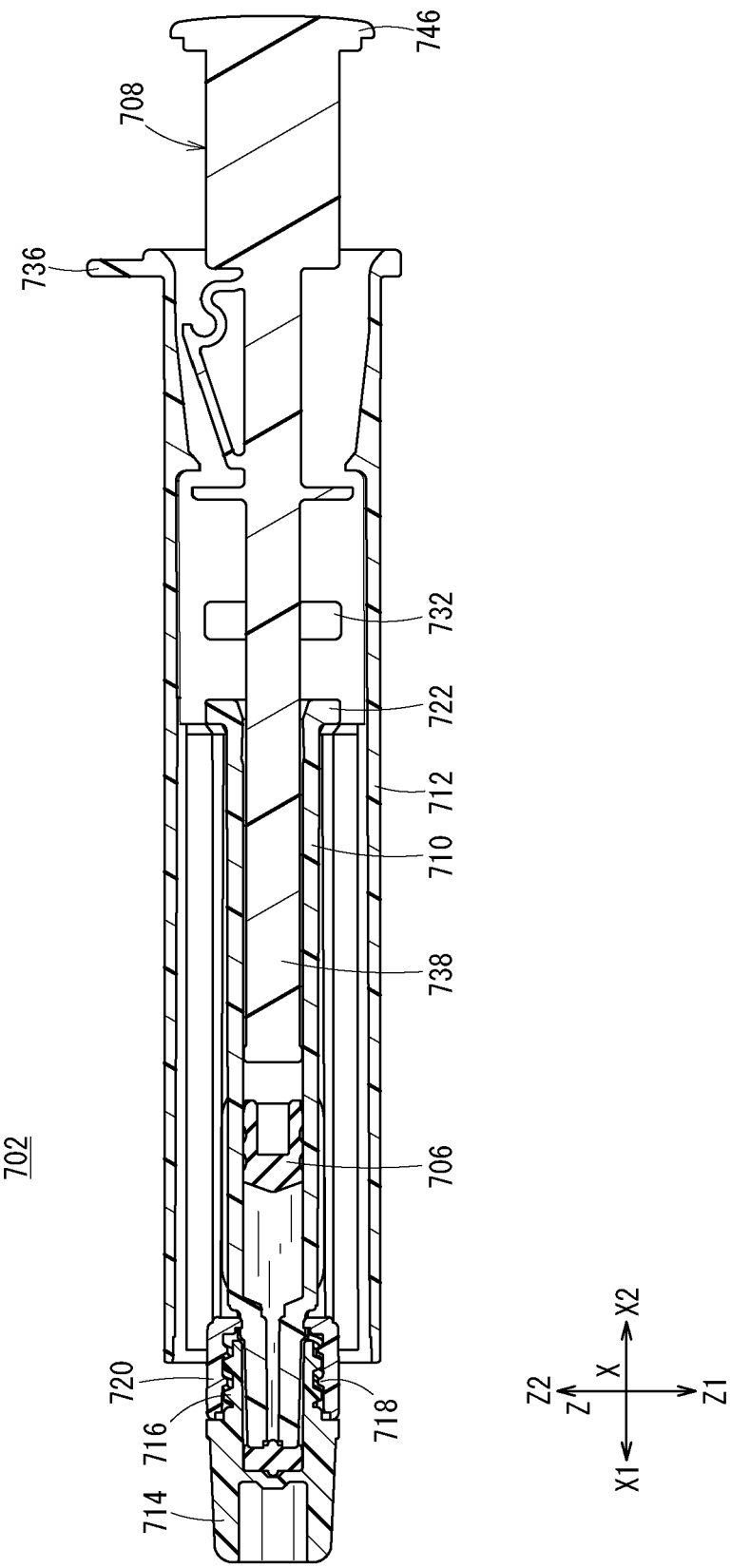
FIG. 3 is a longitudinal sectional view of a prefilled syringe of the syringe packaging body.

As illustrated in FIGS. 2 and 3, the prefilled syringe 702 includes an inner cylinder 710 forming a small-diameter barrel filled with the drug, a gasket 706 provided in the inner cylinder 710, a pusher 708 that pushes the gasket 706 toward a tip end side of the inner cylinder 710, and a large-diameter outer cylinder 712 provided outside the inner cylinder 710.

The inner cylinder 710 is integrally formed of a resin material, glass or the like. The inner cylinder 710 has transparency so that the drug therein may be visually recognized. A tip end of the inner cylinder 710 is formed to be smaller in diameter than a base end side thereof. A sealing cap 714 for sealing an opening on the tip end side of the inner cylinder 710 is detachably mounted on the tip end of the inner cylinder 710. A threaded portion 716 of the sealing cap 714 is threadably mounted on a threaded portion 718 of a connecting unit 720 provided at the tip end of the inner cylinder 710.

The outer cylinder 712 is integrally formed of a resin material. The outer cylinder 712 preferably has transparency so that the drug in the inner cylinder 710 may be easily visually recognized. The outer cylinder 712 is provided coaxially with the inner cylinder 710. A tip end of the outer cylinder 712 is located somewhat closer to a base end than the tip end of the inner cylinder 710. That is, a part of the connecting unit 720 of the inner cylinder 710 is exposed to a tip end side of the outer cylinder 712. Also, the outer cylinder 712 extends toward the base end side from a base end of the inner cylinder 710.

Figure 7:
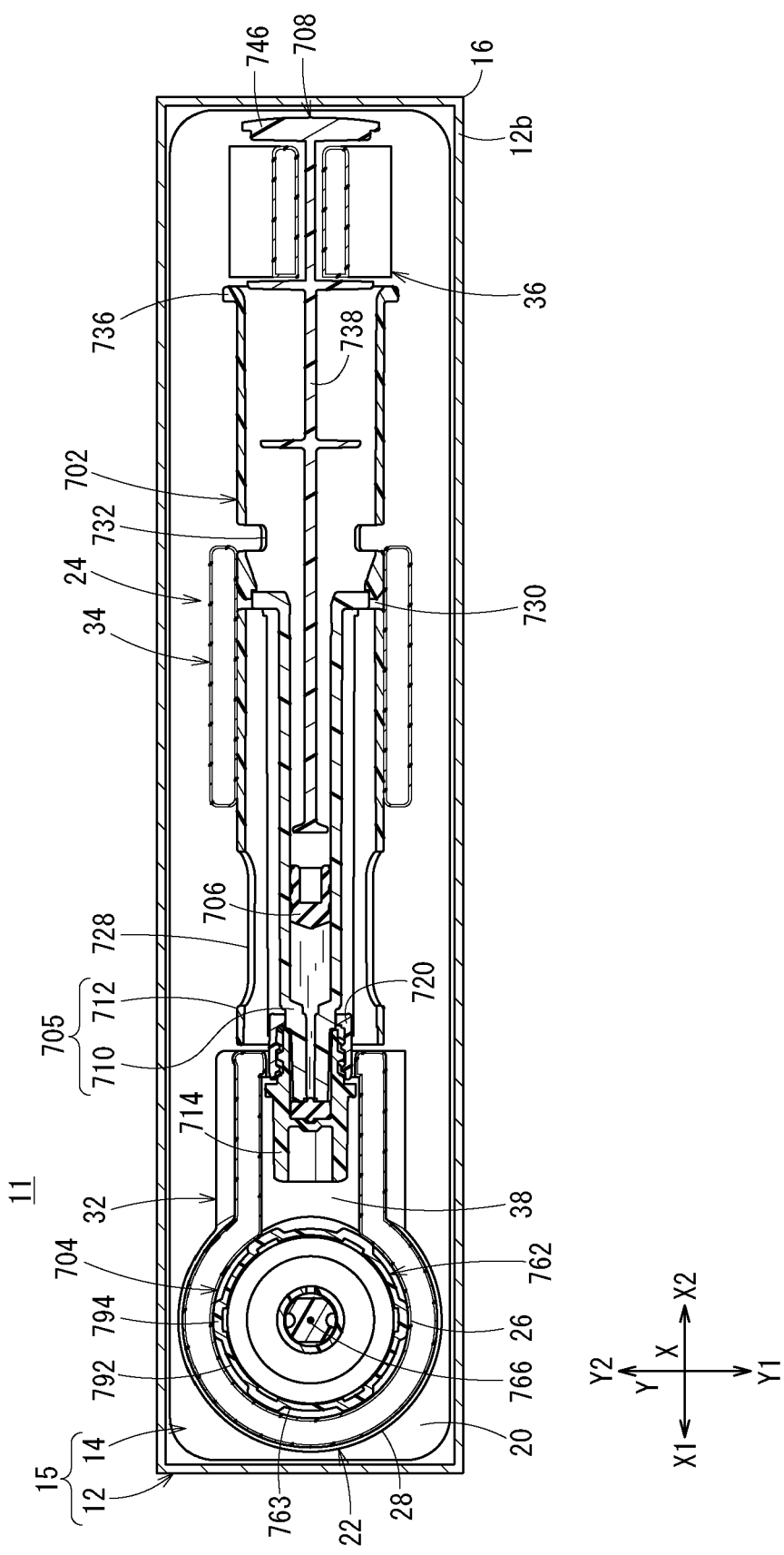
FIG. 7 is a longitudinal sectional view taken along line VII-VII of FIG. 6.

An outer diameter of the outer cylinder 712 is made so as to be easily grasped manually. As illustrated in FIGS. 2 and 7, two first openings 728, two second openings 730, and two third openings 732 are formed so as to be opposed to each other, respectively, on an outer peripheral surface of the outer cylinder 712. The first opening 728, the second opening 730, and the third opening 732 are aligned in an axial direction of the outer cylinder 712. At a base end of the outer cylinder 712, an outer cylinder flange 736 extending radially outward from the outer cylinder 712 is provided.

The gasket 706 is provided so as to be liquid-tightly movable in the axial direction of the inner cylinder 710. That is, the gasket 706 is slidable with respect to an inner peripheral surface of the inner cylinder 710. As a material of the gasket 706, there may be an elastic material including, for example, various rubber materials such as natural rubber, butyl rubber, isoprene rubber, butadiene rubber, styrene-butadiene rubber, and silicone rubber, various thermoplastic elastomers such as a polyurethane type, a polyester type, a polyamide type, an olefin type, and a styrene type, or a mixture thereof.

The pusher 708 is integrally formed of a resin material with a tip end side inserted into the inner cylinder 710 and a base end exposed out of the outer cylinder 712 to the base end side. The pusher 708 includes a shaft portion 738 extending in the axial direction of the inner cylinder 710 and a pusher flange 746 provided at a base end of the shaft portion 738. In an unused state, the pusher 708 is spaced apart from (not connected to) the gasket 706.

Figure 4:
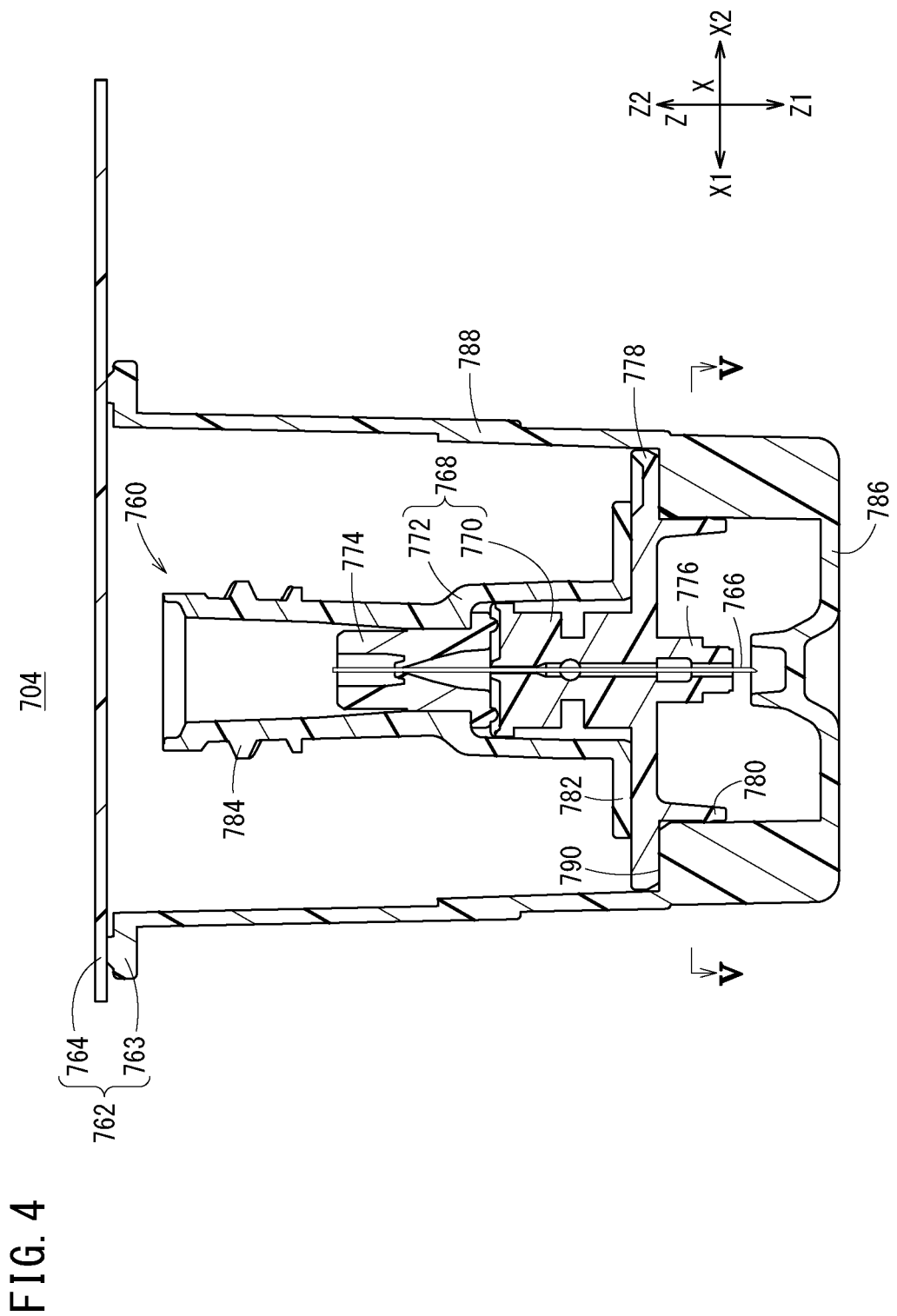
FIG. 4 is a longitudinal sectional view of a needle packaging body of the syringe packaging body.
Figure 5:
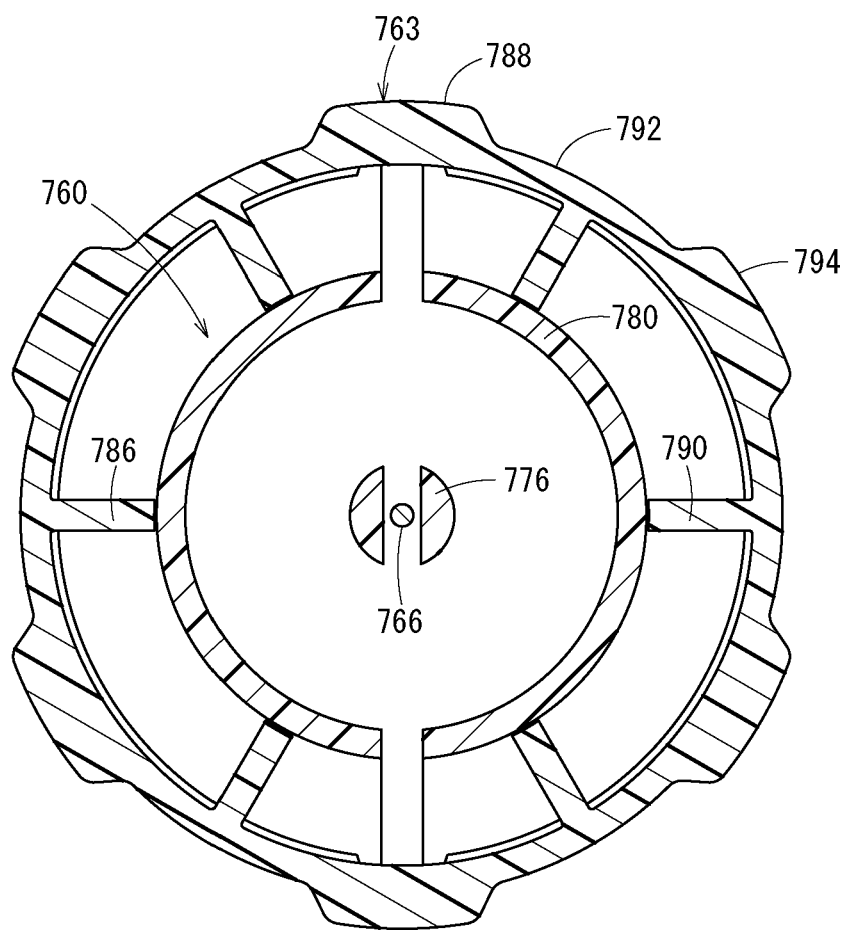
FIG. 5 is a transverse sectional view taken along line V-V of FIG. 4.

As illustrated in FIGS. 2, 4, and 5, the needle packaging body 704 includes the needle unit 760 attachable to the connecting unit 720 of the prefilled syringe 702 and a needle unit case 762 that accommodates the needle unit 760. The needle unit case 762 is provided with a case main body 763 for accommodating the needle unit 760 and a sealing film 764 for sealing the case main body 763. The needle unit 760 includes a tubular needle body 766 including a sharp needle tip at a tip end thereof and a needle hub 768 to which the needle body 766 is fixed. In the following description, in the needle unit 760 and its component, a direction in which the needle tip of the needle body 766 is located is sometimes referred to as a tip end side, and the opposite side is sometimes referred to as a base end side.

The needle body 766 being a hollow tubular member is formed of, for example, a metal material such as stainless steel, aluminum or aluminum alloy, and titanium or a titanium alloy, a hard resin material such as polyphenylene sulfide or the like.

The needle hub 768 includes a first hub 770 that holds the needle body 766, a hollow second hub 772 provided on the first hub 770 and attachable to and detachable from the connecting unit 720 of the prefilled syringe 702, and an elastic member 774 arranged in the second hub 772. Each of the first hub 770 and the second hub 772 is formed of a synthetic resin such as polycarbonate, polypropylene, and polyethylene, for example.

The first hub 770 includes a needle holding unit 776 in which an insertion hole through which the needle body 766 is inserted is formed, an annular collar portion (largest outer diameter portion) 778 projecting radially outward from a tip end side of the needle holding unit 776, and an annular portion 780 extending toward the tip end side from the collar portion 778.

A tip end of the needle holding unit 776 is located in the annular portion 780. A projecting length of the needle body 766 from the tip end of the needle holding unit 776 is preferably set to 0.9 mm to 1.4 mm, for example, in order to surely administer the drug intradermally (in the dermis). The collar portion 778 formed into a plate shape is a portion having the largest diameter of the needle hub 768. The collar portion 778 is located in the vicinity of a tip end of the needle body 766.

The annular portion 780 is formed into an annular shape so as to cover the tip end of the needle holding unit 776 in a peripheral direction. In the axial direction of the needle body 766, a projecting end face of the annular portion 780 is substantially in the same position as a tip end face of the needle holding unit 776. An outer diameter of the annular portion 780 is smaller than an outer diameter of the collar portion 778.

The second hub 772 is a tubular member extending in the axial direction of the needle body 766 with an annular flange 782 provided at a tip end. The second hub 772 is fixed to the first hub 770 in a state in which a base end side of the needle holding unit 776 is inserted into a tip end side of an inner hole thereof and the flange 782 is in contact with the collar portion 778. At a base end side of the inner hole of the second hub 772, the tip end of the inner cylinder 710 of a syringe main body 705 is inserted. A threaded portion 784 to be threadably mounted on the threaded portion of the connecting unit 720 is formed on an outer peripheral surface on a base end side of the second hub 772.

The elastic member 774 is located on the base end side of the needle holding unit 776 of the inner hole of the second hub 772. An insertion hole through which a base end of the needle body 766 is inserted is formed on the elastic member 774. The elastic member 774 is a sealing member that liquid-tightly comes into contact with the outer peripheral surface of the needle body 766 and the inner peripheral surface of the second hub 772 in a state in which the second member is mounted on the connecting unit 720 of the prefilled syringe 702.

The needle unit case 762 has a substantially U-shaped cross section. Specifically, the needle unit case 762 includes a circular bottom surface portion 786 and a peripheral wall portion 788 provided on an outer edge of the bottom surface portion 786. The peripheral wall portion 788 is tapered such that a diameter thereof gradually decreases toward the bottom surface portion 786. On an inner surface of the peripheral wall portion 788, a plurality of engaging convex portions 790 to be engaged with the collar portion 778 is provided at regular intervals in the peripheral direction (refer to FIG. 5).

Each of the engaging convex portions 790 projects radially inward from the inner surface of the peripheral wall portion 788 and is in contact with a surface oriented to a needle tip side of the needle body 766 of the collar portion 778. That is, the needle unit 760 is fixed in the needle unit case 762 with the collar portion 778 fitted to the inner surface of the peripheral wall portion 788 and the annular portion 780 fitted to a space inside a plurality of engaging convex portions 790.

On an outer surface of the peripheral wall portion 788, a plurality of (in FIG. 5, six) concave portions 792 and convex portions 794 extending in the axial direction of the needle body 766 are alternately provided in the peripheral direction. The sealing film 764 is provided so as to block an opening of the needle unit case 762.

When using the prefilled syringe system 700 configured in this manner, first, the sealing cap 714 of the prefilled syringe 702 is removed, and the sealing film 764 of the needle packaging body 704 is peeled off. Then, the threaded portion 718 of the connecting unit 720 of the prefilled syringe 702 is threadably mounted on the threaded portion 784 of the second hub 772 of the needle unit 760 in a state in which the needle unit 760 is located in the needle unit case 762, thereby connecting the needle unit 760 to the prefilled syringe 702.

Thereafter, the needle unit 760 is taken out from the needle unit case 762 and the needle tip is located in the skin by puncture of the needle body 766 on the skin of the living body with the outer cylinder 712 gripped. Subsequently, the pusher flange 746 is pushed toward the tip end side by a thumb. Then, the pusher 708 is brought into contact with the gasket 706 and the gasket 706 is displaced to the tip end side, so that the drug in the inner cylinder 710 is intradermally injected via an inner hole of the needle body 766. After intradermally injecting the drug, the needle body 766 is removed from the skin.

As illustrated in FIG. 2, the packaging unit 15 includes a box-shaped packaging main body 12 and a supporting unit 14 provided in the packaging main body 12 to support the prefilled syringe system 700. The packaging main body 12 is formed of paper into a rectangular parallelepiped shape. However, the packaging main body 12 may also be formed of a material other than paper such as a resin.

The packaging main body 12 includes a packaging basal portion 16 and a lid portion 18 provided so as to be openable with respect to the packaging basal portion 16. The packaging basal portion 16 forms a bottom surface 12a and a side surface 12b of the packaging main body 12 and the lid portion 18 forms a top surface 12c and a part of the side surface 12b in an arrow Y1 direction of the packaging main body 12. In an example in FIG. 2, the packaging main body 12 extends longitudinally in an arrow X direction, the bottom surface 12a is located in an arrow Z1 direction, and the top surface 12c is located in an arrow Z2 direction.

The supporting unit 14 is formed by vacuum molding or pressure molding of a resin material. The resin material forming the supporting unit 14 includes, for example, butadiene-styrene (BS), acrylonitrile-ethylene-propylene-diene-styrene (AES), polycarbonate (PC), polypropylene (PP), polyethylene (PE), polystyrene (PS), high impact polystyrene (HIPS), polyethylene terephthalate (PET), polyvinyl chloride (PVC) and the like.

Figure 6:
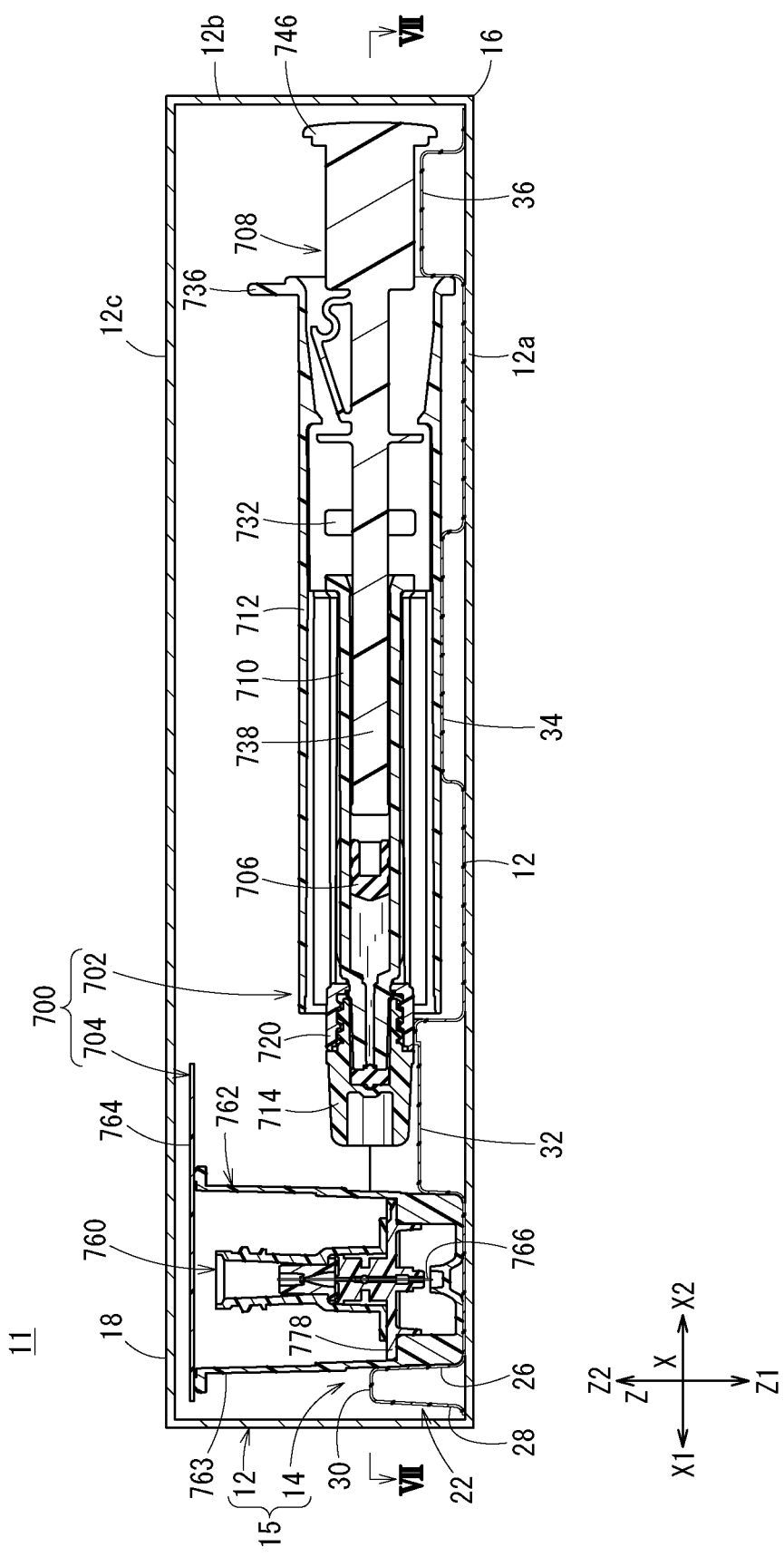
FIG. 6 is a longitudinal sectional view of the syringe packaging body.

As illustrated in FIGS. 2, 6, and 7, the supporting unit 14 includes a plate-shaped base portion 20 extending in the longitudinal direction of the packaging main body 12, a needle unit case supporting unit 22 that supports the needle unit case 762 of the needle packaging body 704, and a syringe supporting unit 24 that supports the prefilled syringe 702. The base portion 20 is placed on the bottom surface 12a in a state of being formed to have substantially the same size as the bottom surface 12a of the packaging main body 12. That is, displacement of the base portion 20 is restricted in a direction parallel to the bottom surface 12a (arrow X direction and arrow Y direction) by the side surface 12b of the packaging main body 12. In other words, the base portion 20 holds the positions of the needle unit case supporting unit 22 and the syringe supporting unit 24 in the packaging main body 12.

The needle unit case supporting unit 22 includes an inner peripheral surface portion 26 and an outer peripheral surface portion 28 that project from an end on one end side (in arrow X1 direction) of the base portion 20 to a side opposite to the bottom surface 12a (in arrow Z2 direction) and a top portion 30 connecting projecting ends of the inner peripheral surface portion 26 and the outer peripheral surface portion 28. The inner peripheral surface portion 26 is formed into an annular shape.

The projecting end in the arrow X2 direction of the inner peripheral surface portion 26 is cut out. The outer peripheral surface portion 28 is formed into a substantially C shape in a planar view. A projecting length of the needle unit case supporting unit 22 is set to approximately one third of an entire length of the needle unit case 762. However, the projecting length of the needle unit case supporting unit 22 may be arbitrarily set.

The syringe supporting unit 24 includes a tip end side supporting unit (tip end side restricting unit) 32 that supports the tip end side of the prefilled syringe 702, an intermediate supporting unit (positional shift restricting unit) 34 that supports an intermediate portion of the prefilled syringe 702, and a base end side supporting unit (displacement restricting unit) 36 that supports the base end side of the prefilled syringe 702.

A tip end side concave portion 38 in which the connecting unit 720 is inserted is formed on the tip end side supporting unit 32. An intermediate concave portion 40 in which the outer cylinder 712 is inserted is formed on the intermediate supporting unit 34. A base end side concave portion 42 in which the pusher 708 is inserted is formed on the base end side supporting unit 36.

In the syringe packaging body 11 configured in this manner, the needle packaging body 704 is inserted inside the inner peripheral surface portion 26 of the needle unit case supporting unit 22. Specifically, the needle unit case 762 is inserted inside the inner peripheral surface portion 26. Then, the inner peripheral surface portion 26 is pushed out (elastically deformed) by the needle unit case 762, so that restoring force (elastic force) of the peripheral wall portion 788 acts on the outer surface of the peripheral wall portion 788 of the needle unit case 762. As a result, displacement in the arrow X direction, arrow Y direction, and arrow Z direction of the needle packaging body 704 with respect to the supporting unit 14 is restricted by the needle unit case supporting unit 22. In other words, the needle packaging body 704 is held by the needle unit case supporting unit 22. On the other hand, the prefilled syringe 702 is attached to the tip end side supporting unit 32, the intermediate supporting unit 34, and the base end side supporting unit 36.

As illustrated in FIG. 1, the outer box 13 is configured as a rectangular parallelepiped shape shipping box for transporting a plurality of syringe packaging bodies 11, and is provided with an outer box main body 90, a partition member 92 that partitions the inside of the outer box main body 90 in a lattice pattern, and a lid portion 94 provided so as to be openable with respect to the outer box main body 90. The outer box main body 90 forms a bottom surface 13a and a side surface 13b of the outer box 13, and the lid portion 94 forms a top surface 13c of the outer box 13. On each side surface 13b of the outer box main body 90, a display unit 96 that displays an up-and-down direction of the outer box 13 at the time of transportation is provided. In FIG. 1, an arrow and a character indicating an upper part of the outer box 13 are illustrated as the display unit 96. That is, the outer box 13 is transported such that the direction indicated by the arrow is vertically upward (in arrow Z2 direction). However, a form, a position, and a size of the display unit 96 may be arbitrarily set.

A plurality of (12 in an example in FIG. 1) accommodating chambers 97 is formed in the outer box main body 90 by the partition member 92. In each accommodating chamber 97, two syringe packaging bodies 11 are accommodated so as to be stacked such that an axis of the needle body 766 is in the up-and-down direction of the outer box 13 (arrow Z direction).

Specifically, in this state, the syringe packaging body 11 is such that the needle tip of the needle body 766 faces a lower part of the outer box 13 (arrow Z1 direction). However, the number of syringe packaging bodies 11 accommodated in each accommodating chamber 97 and the number of accommodating chambers 97 formed in the outer box main body 90 may be arbitrarily set.

A length dimension of each accommodating chamber 97 in the arrow X direction is substantially the same as a dimension in the longitudinal direction of the packaging main body 12, and a width dimension of each accommodating chamber 97 in the arrow Y direction is substantially the same as a width dimension of the packaging main body 12. That is, the displacement of the syringe packaging body 11 in the arrow X direction and arrow Y direction with respect to the outer box 13 in the state of being accommodated in the accommodating chamber 97 is restricted by wall surfaces forming the accommodating chamber 97.

According to this embodiment, because the axial direction of the needle body 766 is in the up-and-down direction of the outer box 13, the axial direction of the needle body 766 is in the vertical direction at the time of transportation. Therefore, it is possible to inhibit the same from being unfixed from the needle unit case 762 when an impact in the vertical direction is applied to the outer box 13 at the time of transportation.

A plurality of syringe packaging bodies 11 is arranged in each accommodating chamber 97 of the outer box 13 so that the needle tip of the needle body 766 faces the lower part of the outer box 13. Therefore, it is possible to effectively inhibit the needle unit 760 from being unfixed from the needle unit case 762 when the outer box 13 drops.

Also, because the prefilled syringe system 700 is supported by the supporting unit 14 provided in the packaging main body 12, positional shift of the needle unit case 762 with respect to the packaging main body 12 may be inhibited. Furthermore, because the needle unit case 762 is supported by the needle unit case supporting unit 22 and the position of the needle unit case supporting unit 22 in the packaging main body 12 is held by the base portion 20, it is possible to inhibit the positional shift of the needle unit case 762 with respect to the packaging main body 12 by a simple configuration.

In this embodiment, displacement of the needle unit case 762 in a direction orthogonal to an extending direction (arrow Z direction) of the needle body 766 with respect to the packaging main body 12 (arrow X direction and arrow Y direction) is restricted by the needle unit case supporting unit 22. Therefore, it is possible to inhibit the needle unit case 762 from falling so that the needle body 766 extends in a horizontal direction within the packaging main body 12 due to vibration at the time of transportation.

Also, because the display unit 96 displaying the up-and-down direction of the outer box 13 is provided on each side surface 13*b* of the outer box 13, the axial direction of the needle body 766 may be surely made in the vertical direction at the time of transportation.

Second Embodiment

Next, a medical equipment package 10B according to a second embodiment of the present invention is described. Note that, in the medical equipment package 10B according to the second embodiment, the same components as those of the medical equipment package 10A according to the first embodiment are assigned with the same reference signs, and the detailed description thereof is omitted. The same applies to medical equipment packages 10C and 10D according to third and fourth embodiments, respectively, to be described later.

Figure 8:
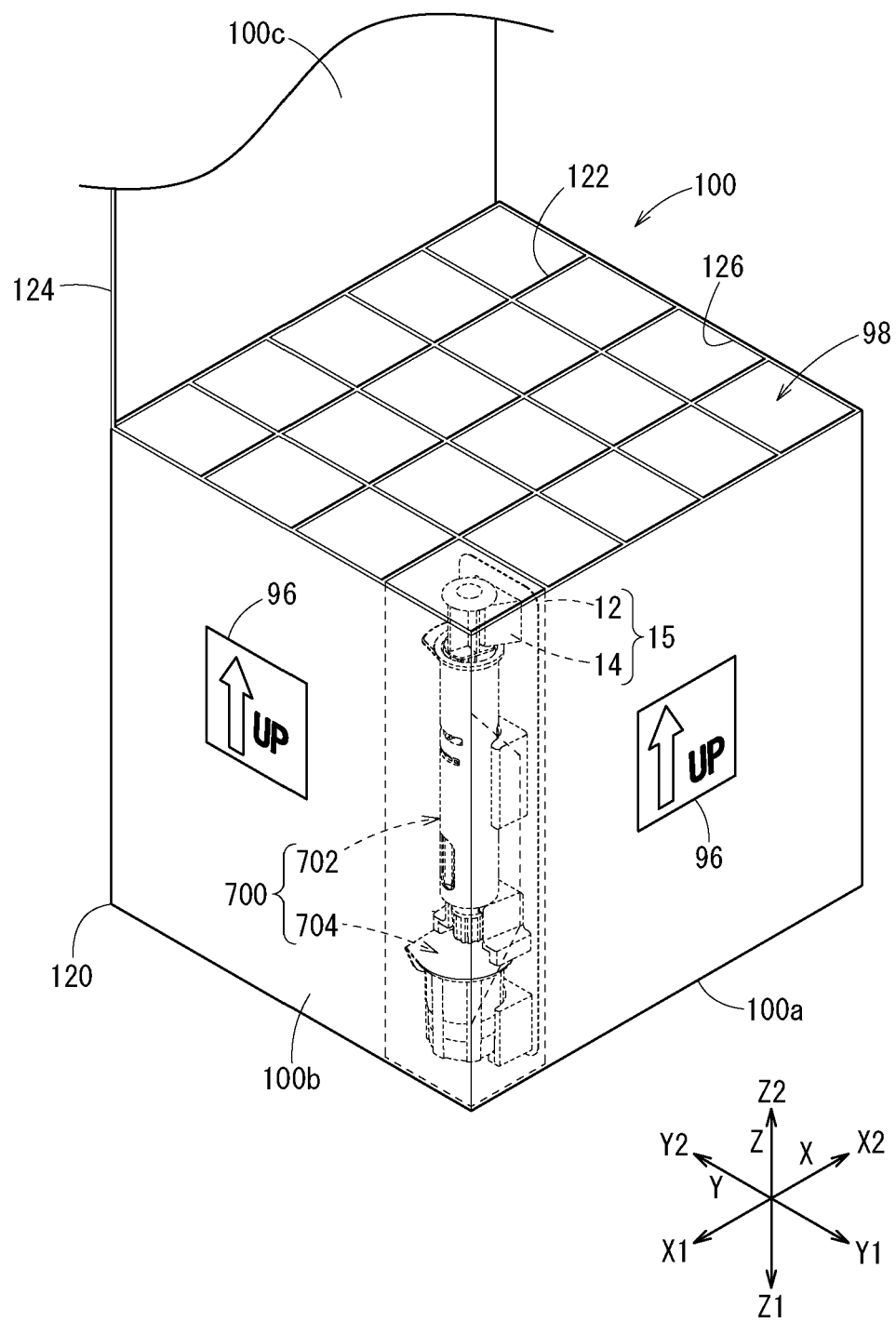
FIG. 8 is a perspective view of a medical equipment package according to a second embodiment of the present invention.
Figure 9:
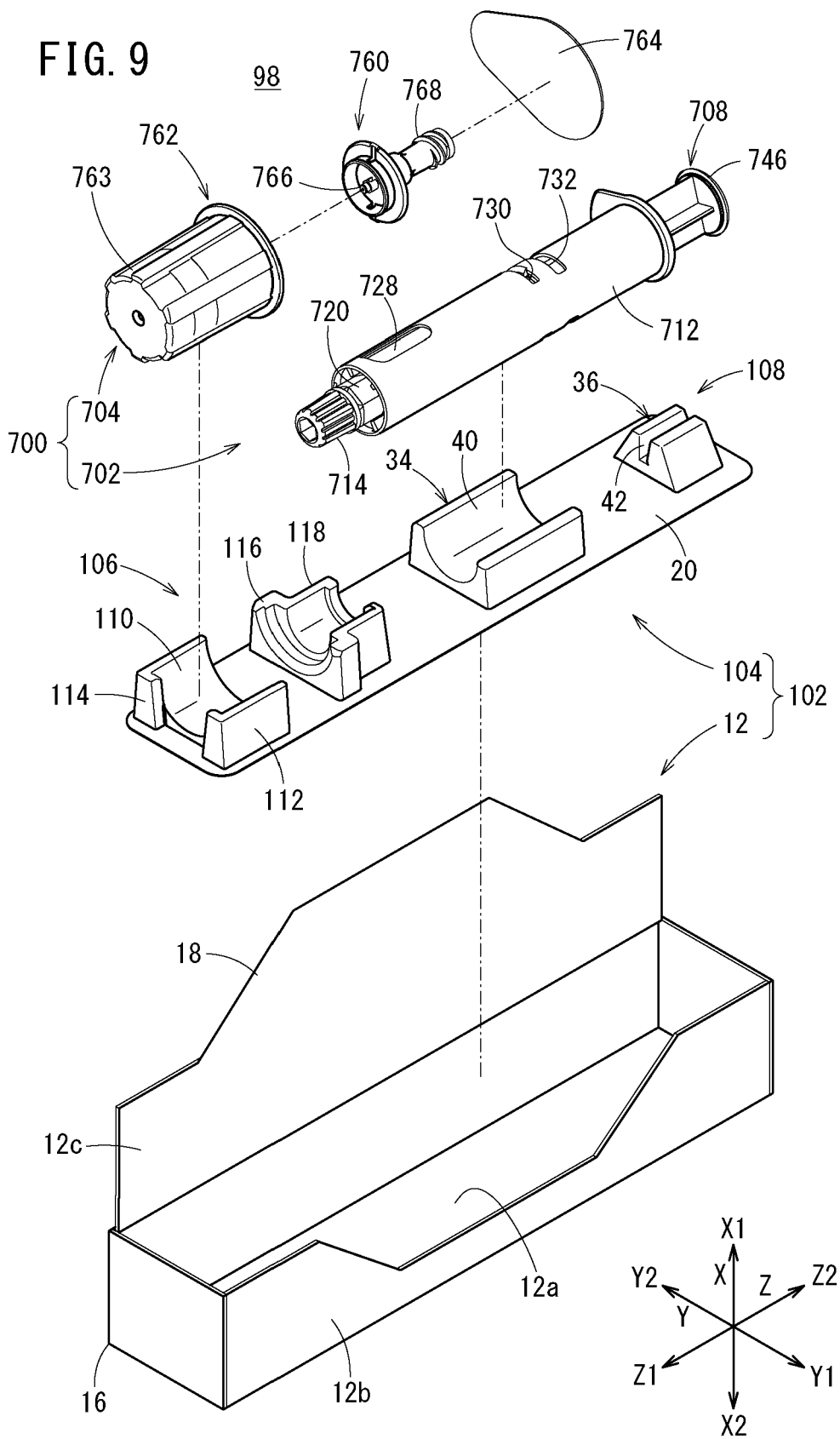
FIG. 9 is an exploded perspective view of the syringe packaging body illustrated in FIG. 8.

As illustrated in FIG. 8, the medical equipment package 10B according to this embodiment is provided with an outer box 100 that accommodates a plurality of syringe packaging bodies 98. As illustrated in FIGS. 9 and 10, the syringe packaging body 98 includes a prefilled syringe system 700 and a packaging unit 102 that accommodates the prefilled syringe system 700.

The packaging unit 102 includes a packaging main body 12 and a supporting unit 104 arranged in the packaging main body 12. The supporting unit 104 includes a base portion 20, a needle unit case supporting unit 106 and a syringe supporting unit 108 provided on the base portion 20.

The needle unit case supporting unit 106 supports the needle unit case 762 such that a needle tip of the needle body 766 faces in an arrow Z1 direction. That is, in a state in which the needle unit case 762 is attached to the needle unit case supporting unit 106, the needle body 766 is in an axial direction (arrow Z direction) of the prefilled syringe 702.

The needle unit case supporting unit 106 is provided at an end in the arrow Z1 direction of the base portion 20, and includes a first wall portion 112 in which a supporting concave portion 110 with a circular (substantially semicircular) cross-sectional face in which a bottom portion of a case main body 763 is inserted is formed, a second wall portion 114 that restricts displacement of the needle unit case 762 inserted in the supporting concave portion 110 in the arrow Z1 direction with respect to the supporting unit 104, and a third wall portion 116 that restricts displacement in an arrow Z2 direction of the needle unit case 762 inserted in the supporting concave portion 110 with respect to the supporting unit 104.

The first wall portion 112 restricts displacement of the needle unit case 762 in an arrow Y direction with respect to the supporting unit 104. The second wall portion 114 is continuous to the first wall portion 112. The third wall portion 116 is spaced apart from the first wall portion 112 in the arrow Z2 direction.

The syringe supporting unit 108 is provided with a tip end side supporting unit 118, an intermediate supporting unit 34, and a base end side supporting unit 36. The tip end side supporting unit 118 extends from the third wall portion 116 in the arrow Z2 direction. The tip end side supporting unit 118 is configured similarly to the above-described tip end side supporting unit 32 and supports a connecting unit 720 of a prefilled syringe 702.

As illustrated in FIG. 8, the outer box 100 is provided with an outer box main body 120, a partition member 122 that partitions the inside of the outer box main body 120 in a lattice pattern, and a lid portion 124 provided so as to be openable with respect to the outer box main body 120. The outer box main body 120 forms a bottom surface 100*a* and a side surface 100*b* of the outer box 100, and the lid portion 124 forms a top surface 100*c* of the outer box 100. On each side surface 100*b* of the outer box main body 120, a display unit 96 that defines an up-and-down direction of the outer box 100 is provided.

A plurality of (20 in an example in FIG. 8) accommodating chambers 126 is formed in the outer box main body 120 by the partition member 122. In each accommodating chamber 126, one syringe packaging body 98 is accommodated such that an axis of a needle body 766 is in the up-and-down direction of the outer box 100. In this state, the syringe packaging body 98 is such that a needle tip of the needle body 766 faces a lower part of the outer box 100 (in arrow Z1 direction).

According to this embodiment, the action and effect similar to those of the medical equipment package 10A according to the above-described first embodiment are obtained.

Third Embodiment

Figure 12:
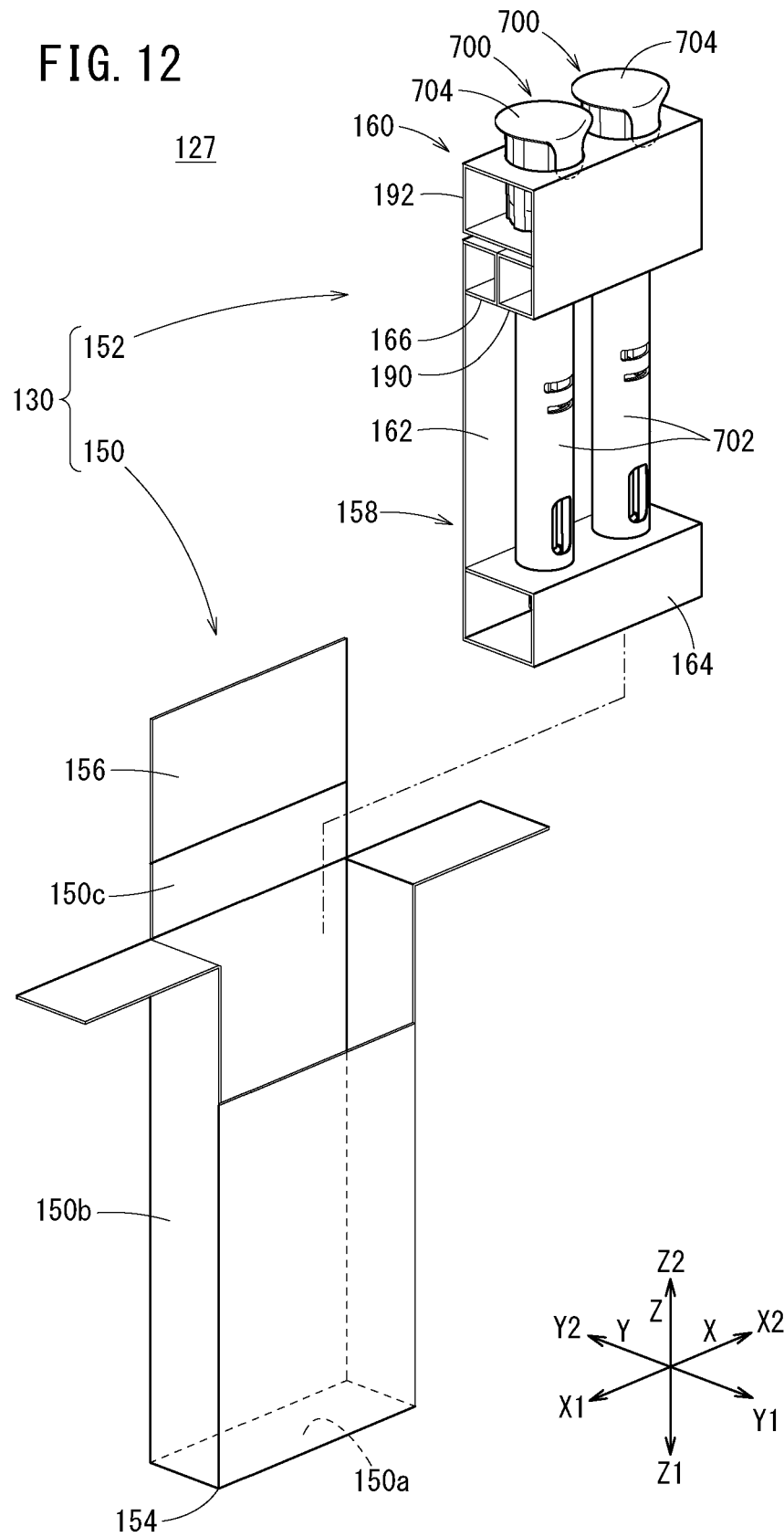
FIG. 12 is an exploded perspective view of a syringe packaging body illustrated in FIG. 11.

Next, a medical equipment package 10C according to a third embodiment of the present invention is described. As illustrated in FIG. 11, the medical equipment package 10C according to this embodiment is provided with an outer box 128 that accommodates a plurality of syringe packaging bodies 127. As illustrated in FIG. 12, the syringe packaging body 127 includes two prefilled syringe systems 700 and a packaging unit 130 that accommodates the prefilled syringe systems 700.

The packaging unit 130 includes a packaging main body 150 and a supporting unit 152 arranged in the packaging main body 150. The packaging main body 150 is formed of paper into a rectangular parallelepiped shape. However, the packaging main body 150 may also be formed of a material other than paper such as a resin. Specifically, the packaging main body 150 includes a packaging basal portion 154 and a lid portion 156 joined so as to be openable with respect to the packaging basal portion 154. The packaging basal portion 154 forms a bottom surface 150*a* and a side surface 150*b* of the packaging main body 150 and the lid portion 156 forms a top surface 150*c* and a part of the side surface 150*b* in an arrow Y1 direction of the packaging main body 150. In an example in FIG. 12, the packaging main body 150 extends longitudinally in an arrow Z direction, the bottom surface 150*a* is located in an arrow Z1 direction, and the top surface 150*c* is located in an arrow Z2 direction.

Figure 13:
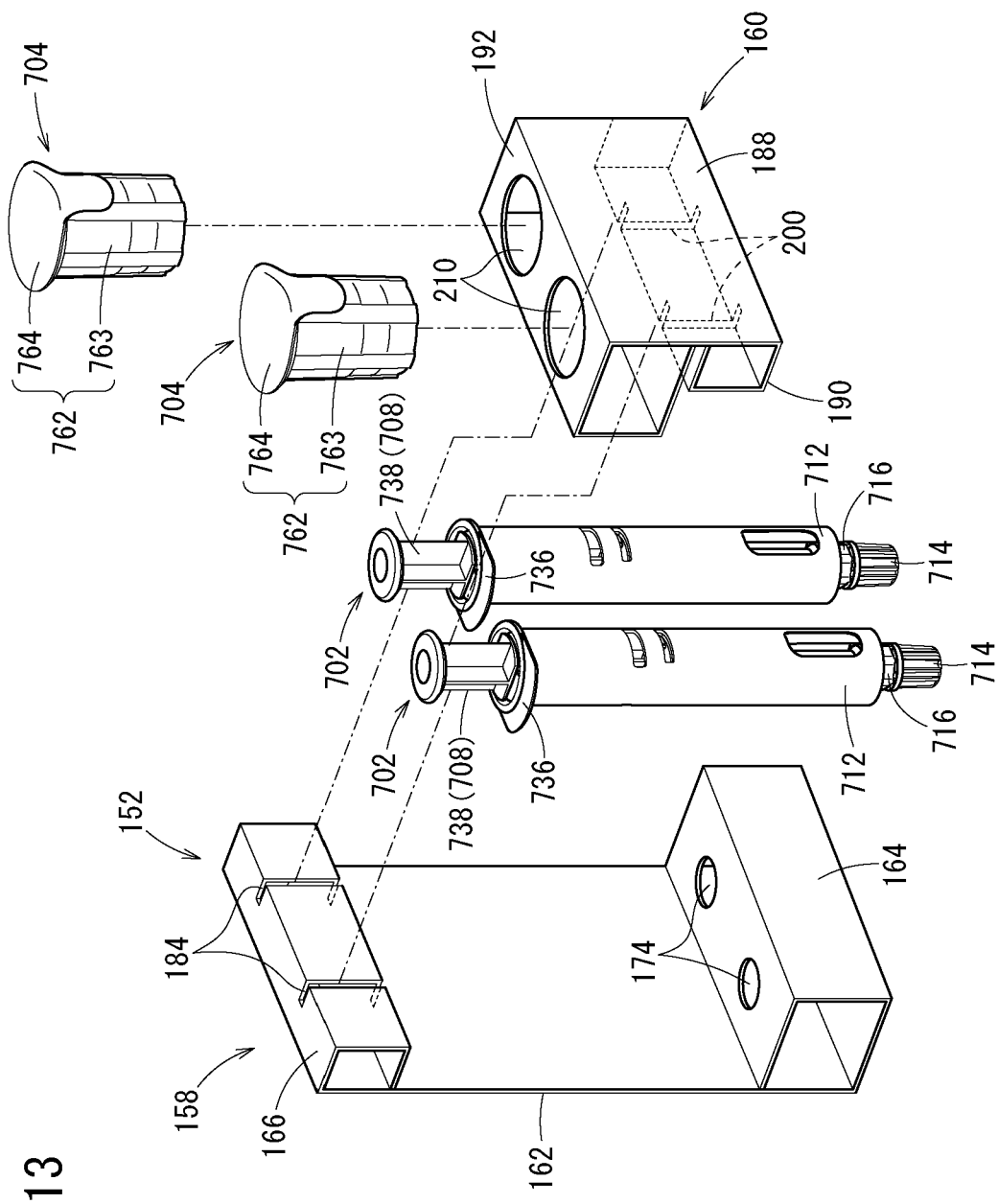
FIG. 13 is an exploded perspective view of a package unit illustrated in FIG. 12.

As illustrated in FIGS. 12 and 13, the supporting unit 152 includes a first support member 158 and a second support member 160. The first support member 158 and the second support member 160 are assembled, for example, by folding paper. The first support member 158 includes a rectangular first base portion 162 extending in an extending direction (arrow Z direction) of the packaging main body 150, a tip end side supporting unit 164 that supports a tip end side of a prefilled syringe 702, and a first base end side supporting unit 166 that supports a base end side of the prefilled syringe 702.

Two syringe support holes 174 through which the connecting units 720 of the prefilled syringes 702 are inserted are formed on the tip end side supporting unit 164 so as to be aligned in the arrow X direction. A diameter of the syringe support hole 174 is smaller than an outer diameter of an outer cylinder 712.

Two first grooves (slits) 184 in which pushers 708 are inserted are formed on the first base end side supporting unit 166 across an entire length in the arrow Z direction. The first grooves 184 are provided so as to be spaced apart from each other in the arrow X direction.

The second support member 160 includes a second base portion 188, a second base end side supporting unit 190 that supports the base end side of the prefilled syringe 702, and a needle supporting unit 192 that supports the needle unit case 762 of the needle packaging body 704. The second base end side supporting unit 190 is formed into a substantially U shape as seen from a side surface 150b, and is opposed to the first base end side supporting unit 166 in the arrow Y direction.

Specifically, a gap in which the pusher flange 746 may be inserted is formed between the second base end side supporting unit 190 and the needle supporting unit 192. Two second grooves (slits) 200 in which shafts 738 of the pushers 708 are inserted are formed on the second base end side supporting unit 190 across an entire length in the arrow Z direction. The second grooves 200 are provided so as to be spaced apart from each other in the arrow X direction.

The needle supporting unit 192 is formed into a substantially U shape in a side view, and is located in a direction opposite to the tip end side supporting unit 164 (arrow Z2 direction) of the first base end side supporting unit 166 and the second base end side supporting unit 190. Two needle unit case supporting units 210 through which the needle unit cases 762 of the needle packaging bodies 704 are inserted are formed side by side in the arrow X direction on a surface oriented in the arrow Z1 direction of the needle supporting unit 192. The needle supporting unit 192 is provided such that a needle tip of a needle body 766 faces in the arrow Z1 direction (prefilled syringe 702 side).

In the medical equipment package 10C configured in this manner, the two prefilled syringes 702 are attached side by side in the arrow X direction and the two needle unit cases 762 are attached side by side in the arrow X direction. Specifically, the connecting unit 720 of the prefilled syringe 702 is inserted in the syringe support hole 174. Also, the pusher flange 746 is arranged between the second base end side supporting unit 190 and the needle supporting unit 192.

The needle unit case 762 is inserted in the needle unit case supporting unit 210. As a result, displacement of the needle unit case 762 with respect to the supporting unit 152 in the arrow X and arrow Y directions is restricted. Note that, the displacement of the needle packaging body 704 in the arrow Z2 direction with respect to the supporting unit 152 is restricted by the top surface 150c of the packaging main body 150.

As illustrated in FIG. 11, the outer box 128 is provided with an outer box main body 201, a partition member 203 that partitions the inside of the outer box main body 201 in a lattice pattern, and a lid portion 205 provided so as to be openable with respect to the outer box main body 201. The outer box main body 201 forms a bottom surface 128a and a side surface 128b of the outer box 128, and the lid portion 205 forms a top surface 128c of the outer box 128. On each outer side surface of the outer box main body 201, a display unit 96 that defines an up-and-down direction of the outer box 128 is provided.

A plurality of (nine in an example in FIG. 12) accommodating chambers 207 is formed in the outer box main body 201 by the partition member 203. In each accommodating chamber 207, one syringe packaging body 127 is accommodated such that an axis of the needle body 766 is in the up-and-down direction of the outer box 128. In this state, the syringe packaging body 127 is such that the needle tip of the needle body 766 faces a lower part of the outer box 128 (arrow Z1 direction).

The medical equipment package 10C according to this embodiment may obtain the action and effect similar to those of the medical equipment package 10A according to the above-described first embodiment.

Fourth Embodiment

Figure 14:
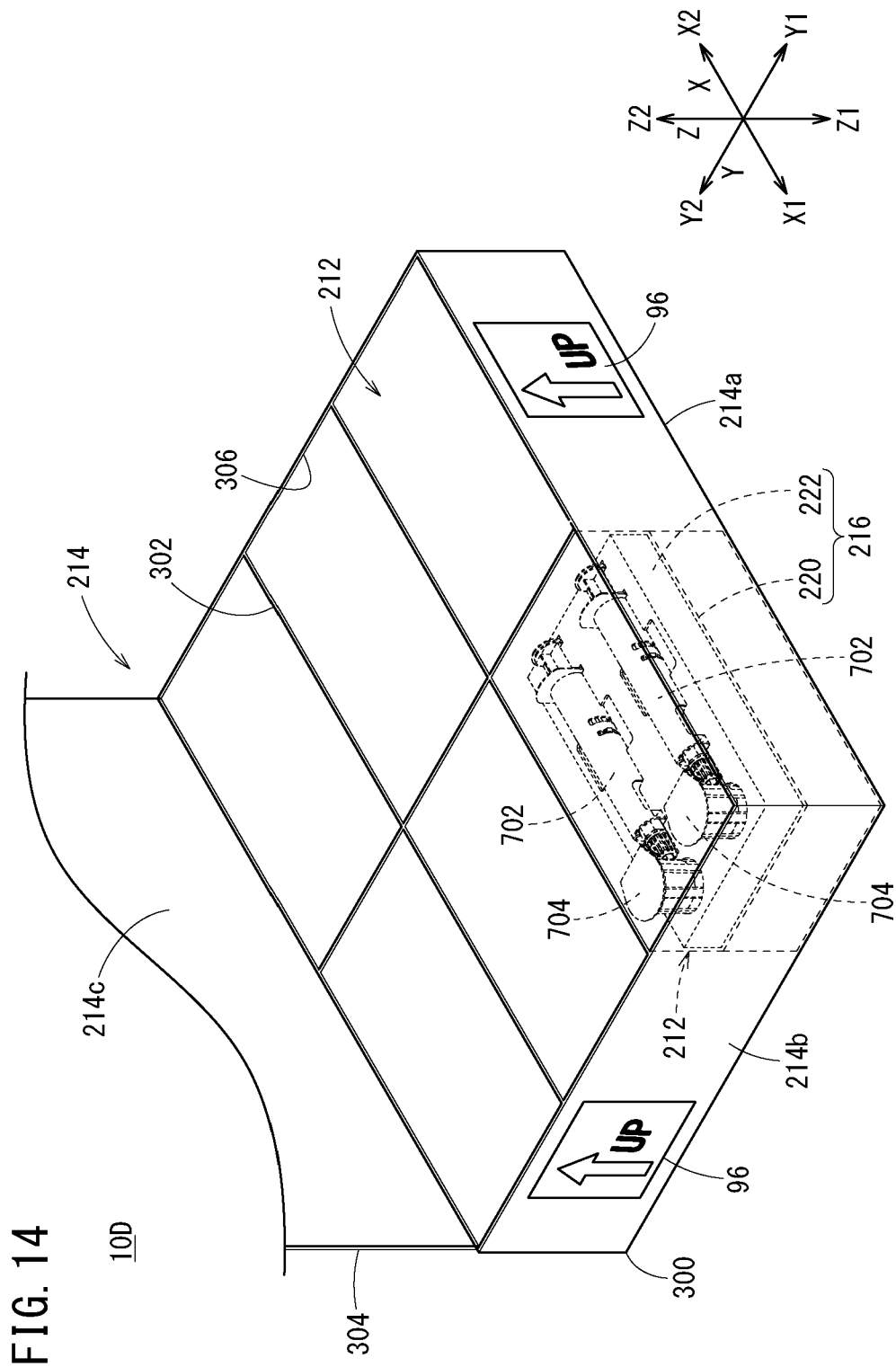
FIG. 14 is a perspective view of a medical equipment package according to a fourth embodiment of the present invention.
Figure 15:
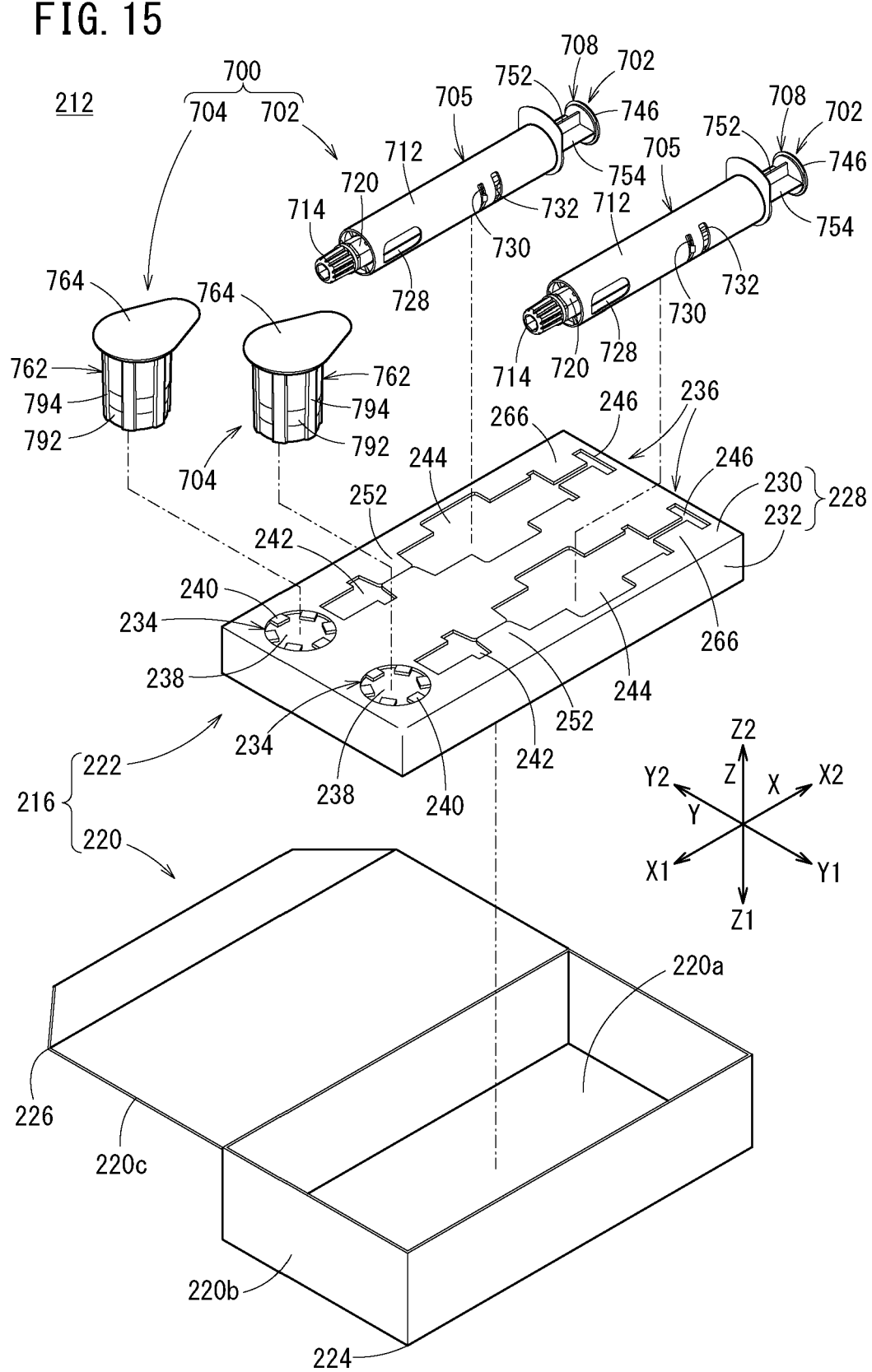
FIG. 15 is an exploded perspective view of the syringe packaging body illustrated in FIG. 14.

Next, a medical equipment package 10D according to a fourth embodiment of the present invention is described. As illustrated in FIG. 14, the medical equipment package 10D according to this embodiment is provided with an outer box 214 that accommodates a plurality of syringe packaging bodies 212. As illustrated in FIG. 15, the syringe packaging body 212 includes two prefilled syringe systems 700 and a packaging unit 216 that accommodates the prefilled syringe systems 700.

The packaging unit 216 includes a packaging main body 220 and a supporting unit 222 arranged in the packaging main body 220. The packaging main body 220 is formed of paper into a rectangular parallelepiped shape. However, the packaging main body 220 may also be formed of a material other than paper such as a resin. Specifically, the packaging main body 220 includes a packaging basal portion 224 and a lid portion 226 joined so as to be openable with respect to the packaging basal portion 224. The packaging basal portion 224 forms a bottom surface 220a and a side surface 220b of the packaging main body 220 and the lid portion 226 forms a top surface 220c and a part of the side surface 220b in an arrow Y1 direction of the packaging main body 220. In an example in FIG. 15, the packaging main body 220 extends longitudinally in an arrow X direction, the bottom surface 220a is located in an arrow Z1 direction, and the top surface 220c is located in an arrow Z2 direction.

Figure 16:
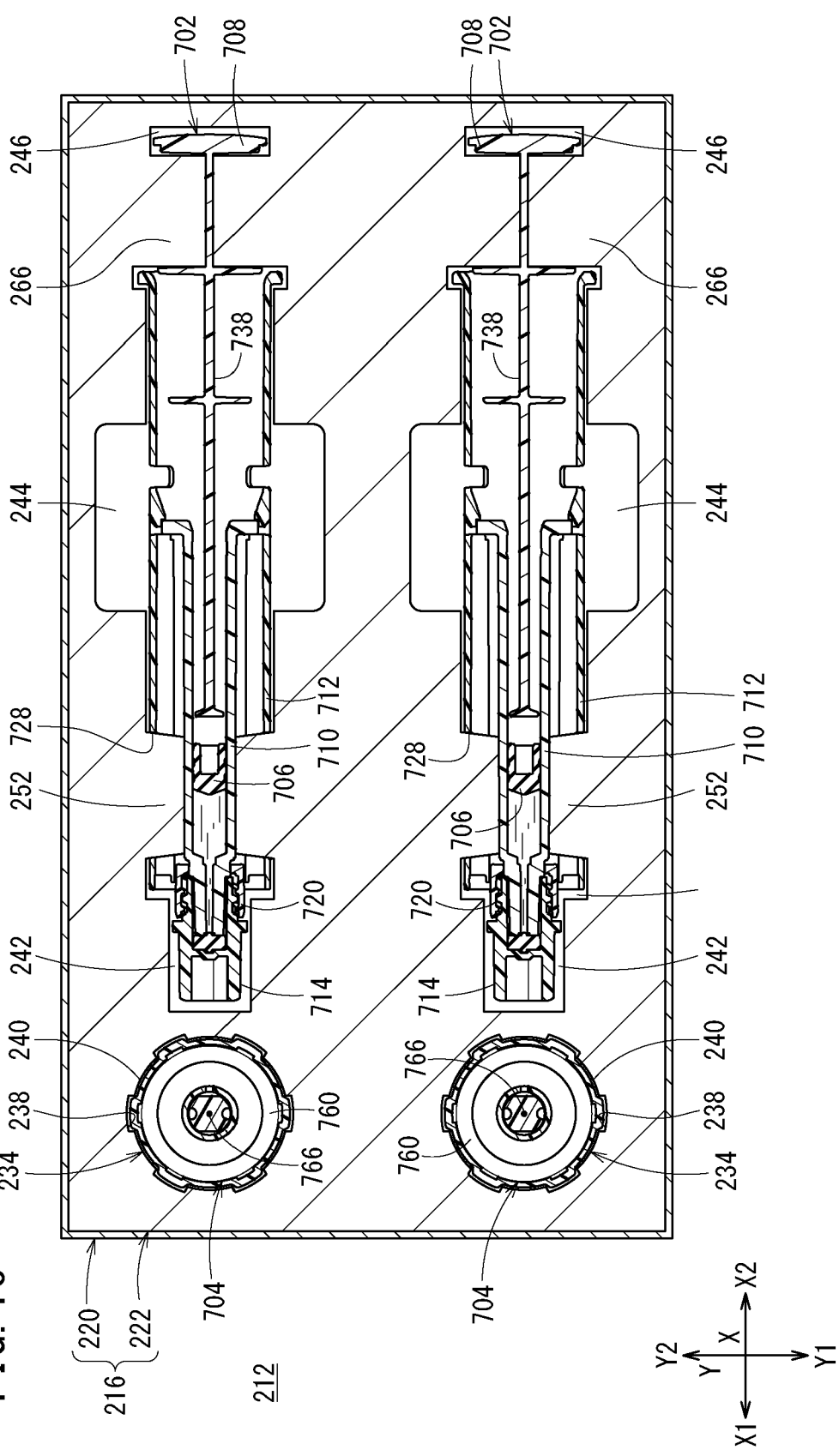
FIG. 16 is a longitudinal sectional view of a syringe packaging body illustrated in FIG. 15.

As illustrated in FIGS. 15 and 16, the supporting unit 222 is provided with a base portion 228 formed of paper. The base portion 228 includes a rectangular base portion main body 230 and a leg portion 232 extending from an outer edge of the base portion main body 230. The base portion main body 230 has substantially the same size as the bottom surface 220a of the packaging main body 220. In other words, the leg portion 232 is brought into contact with each side face 220b of the packaging main body 220. The base portion main body 230 is provided with two needle unit case supporting units 234 that support needle packaging bodies 704 and two syringe supporting units 236 that support prefilled syringes 702.

Each needle unit case supporting unit 234 includes a needle unit case support hole 238 formed at one end in a longitudinal direction (end in arrow X1 direction) of the base portion main body 230. The two needle unit case support holes 238 are located at a predetermined interval in a width direction (arrow Y direction) of the base portion main body 230. A plurality of projections 240 extending toward the center (radially inward) of the needle unit case support hole 238 is provided at regular intervals in a peripheral direction on a wall surface forming each needle unit case support hole 238. The projections 240 are to be inserted in concave portions 792 of the needle unit case 762. Therefore, the number and positions of the projections 240 correspond to the number of the concave portions 792 of the needle unit case 762.

Each syringe supporting unit 236 includes a tip end side supporting unit 242 that is a hole in which a tip end side of the prefilled syringe 702 is inserted, an intermediate supporting unit 244 that is a hole in which an intermediate portion of the prefilled syringe 702 is inserted, and a base end side supporting unit 246 that is a hole in which a pusher 708 of the prefilled syringe 702 is inserted.

A connecting unit 720 is inserted in the tip end side supporting unit 242. Two first locking units 252 to be inserted in first openings 728 of the prefilled syringe 702 are provided between the tip end side supporting unit 242 and the intermediate supporting unit 244. In other words, the first locking units 252 are provided so as to be in contact with each other in a state in which the prefilled syringe 702 is not mounted on the supporting unit 222 and partition the tip end side supporting unit 242 from the intermediate supporting unit 244.

A base end side than the first opening 728 of the tip end side of the outer cylinder 712 is inserted in the intermediate supporting unit 244. A shaft portion 738 and a pusher flange 746 of the pusher 708 are inserted in the base end side supporting unit 246.

In the medical equipment package 10D configured in this manner, the two needle packaging bodies 704 are attached side by side in the arrow Y direction and the two prefilled syringes 702 are attached side by side in the arrow Y direction. Specifically, because the needle unit case 762 of the needle packaging body 704 is inserted in the needle unit case support hole 238, displacement in the arrow X and arrow Y directions of the needle packaging body 704 with respect to the supporting unit 222 is restricted by the wall surface forming the needle unit case support hole 238. Also, in this state, the projection 240 is inserted in the concave portion 792 of the needle unit case 762, so that rotation around an axis of the needle packaging body 704 is restricted by the projection 240.

As illustrated in FIG. 14, the outer box 214 is provided with an outer box main body 300, a partition member 302 that partitions the inside of the outer box main body 300 in a lattice pattern, and a lid portion 304 provided so as to be openable with respect to the outer box main body 300. The outer box main body 300 forms a bottom surface 214a and a side surface 214b of the outer box 214, and the lid portion 304 forms a top surface 214c of the outer box 214. On each side surface 214b of the outer box main body 300, a display unit 96 that displays an up-and-down direction of the outer box 214 is provided.

A plurality of (six in an example in FIG. 14) accommodating chambers 306 is formed in the outer box main body 300 by the partition member 302. In each accommodating chamber 306, one syringe packaging body 212 is accommodated with its longitudinal direction oriented in the Y arrow direction. That is, in this state, the axis of the needle body 766 of the syringe packaging body 212 is in the arrow Z direction. In other words, in this state, the syringe packaging body 212 is such that the needle tip of the needle body 766 faces a lower part of the outer box 214 (arrow Z1 direction).

The medical equipment package 10D according to this embodiment may obtain the action and effect similar to those of the medical equipment package 10A according to the above-described first embodiment.

It goes without saying that the medical equipment package according to the present invention is not limited to the above-described embodiments, and various configurations may be adopted without departing from the gist of the present invention.

REFERENCE NUMERAL LIST 10A to 10D Medical equipment package
11, 98, 127, 212 syringe packaging body
12, 150, 220 Packaging main body
13, 100, 128, 214 Outer box
700 Prefilled syringe system
702 Prefilled syringe
704 Needle packaging body
760 Needle unit
762 Needle unit case
766 Needle body
768 Needle hub
778 Collar portion (largest outer diameter portion)

What is claimed is:

1. A medical equipment package containing a plurality of prefilled syringe systems, the medical equipment package comprising:
   a plurality of syringe packaging bodies, each of the syringe packaging bodies comprising a packaging main body that accommodates one of the prefilled syringe systems; and
   an outer box that accommodates the plurality of syringe packaging bodies, the outer box comprising:
      an outer box main body that forms a bottom surface and a side surface of the outer box, and
      a lid portion that forms a top surface of the outer box and that is openable with respect to the outer box main body;
   wherein each prefilled syringe system comprises:
      a prefilled syringe,
      a needle packaging body comprising:
         a needle unit that comprises a needle body configured to puncture a living body, and a needle hub that holds the needle body, wherein the needle hub comprises an annular collar, and
         a needle unit case that accommodates the needle unit;
   wherein the needle unit is supported with respect to the needle unit case such that a bottom surface of the annular collar engages with an radially inward extending surface of the needle unit case that at least partially opposes the bottom surface of the annular collar; and
   wherein the plurality of syringe packaging bodies are arranged in the outer box such that an axial direction of each needle body is perpendicular to the bottom surface of the outer box and such that a needle tip of each needle body faces in a direction toward the bottom surface of the outer box.

2. The medical equipment package according to claim 1, wherein:
   each of the syringe packaging bodies further comprises a supporting unit arranged in the packaging main body and supporting a respective one of the prefilled syringe systems.

3. The medical equipment package according to claim 2, wherein:
   each supporting unit comprises:
      a needle unit case supporting unit that supports a respective one of the needle unit cases, and
      a base portion that holds a position of the needle unit case supporting unit in the packaging main body.

4. The medical equipment package according to claim 3, wherein:
   the needle unit case supporting unit restricts displacement in a direction orthogonal to the axial direction of a respective one of the needle bodies with respect to the packaging main body of the needle unit case.

5. The medical equipment package according to claim 1, wherein:

an image displaying an up-and-down direction as a direction parallel to the axial direction of each needle body is provided on an outer surface of the outer box.

6. The medical equipment package according to claim 1, wherein:
the needle unit case comprises:
a peripheral wall portion, and
a plurality of convex portions extending radially inward from an inner surface of the peripheral wall portion,
the bottom surface of the annular collar engages top surfaces of the convex portions.

7. The medical equipment package according to claim 6, wherein:
the needle unit further comprises an annular portion extending in an axial direction from the bottom surface of the annular collar,
wherein an outer diameter of the annular portion is less than an outer diameter of the annular collar.

8. The medical equipment package according to claim 7, wherein:
inner surfaces of the convex portions contact an outer circumferential surface of the annular portion.

* * * * *